(12) United States Patent
Kuchimanchi et al.

(10) Patent No.: US 12,193,464 B2
(45) Date of Patent: Jan. 14, 2025

(54) ORGANIC NATURAL MICROBIAL INHIBITOR

(71) Applicants: Venkata Satya Sarveswara Sairam Kuchimanchi, Secunderabad (IN); Vaishnavi Kuchimanchi, Secunderabad (IN)

(72) Inventors: Venkata Satya Sarveswara Sairam Kuchimanchi, Secunderabad (IN); Vaishnavi Kuchimanchi, Secunderabad (IN)

( * ) Notice: Subject to any disclaimer, the term of this patent is extended or adjusted under 35 U.S.C. 154(b) by 622 days.

(21) Appl. No.: 17/432,624

(22) PCT Filed: Oct. 2, 2019

(86) PCT No.: PCT/IN2019/050727
§ 371 (c)(1),
(2) Date: Aug. 20, 2021

(87) PCT Pub. No.: WO2020/240574
PCT Pub. Date: Dec. 3, 2020

(65) Prior Publication Data
US 2022/0159999 A1  May 26, 2022

(30) Foreign Application Priority Data

May 28, 2019 (IN) .............................. 201941021081

(51) Int. Cl.
*A23L 3/3508* (2006.01)
*A01N 37/02* (2006.01)
(Continued)

(52) U.S. Cl.
CPC ............ *A23L 3/3508* (2013.01); *A01N 37/02* (2013.01); *A01N 63/20* (2020.01); *A01P 1/00* (2021.08);
(Continued)

(58) Field of Classification Search
None
See application file for complete search history.

(56) References Cited

FOREIGN PATENT DOCUMENTS

WO    WO 2007/031186 A1    3/2007

OTHER PUBLICATIONS

Ozcelik, Sezen; et al; "Formation of lactic, acetic, succinic, propionic, formic and butyric acid by lactic acid bacteria" LWT—Food Science and Technology, 73, 536-542, 2016 (Year: 2016).*

(Continued)

*Primary Examiner* — David W Berke-Schlessel
(74) *Attorney, Agent, or Firm* — Hamilton, Brook, Smith & Reynolds, P.C.

(57) ABSTRACT

Nowadays consumers are looking for "natural" food ingredients for keeping them healthy and fit in all foods. "An Organic Natural Microbial Inhibitor" is an organic antimicrobial ingredient that is synthesized from the fermentation of natural raw materials including rice flour, wheat hydrolysate and corn steep liquor. An amount of 0.1 to 1.5% during preservation of different food products like pickles, salads, beverages, and meat etc., keeps the food free from the microbial contaminations, increases flavor, and meat tenderness. It is produced through co-fermentation of *Acetobacter aceti* and *Lactobacillus delbrueckii* that are modified by way of strain improvement through medium optimization experiments. The major ingredients of the product include combination of naturally produced organic acids like acetic, lactic and propionic acids in addition to other acids in trace amounts in liquid form and also in powdered form. These are in combination responsible for the antimicrobial property with simultaneous flavor enhancement.

14 Claims, 6 Drawing Sheets

(51) Int. Cl.
*A01N 63/20* (2020.01)
*A01P 1/00* (2006.01)
*A23B 4/26* (2006.01)
*A23L 3/358* (2006.01)
*A23L 33/16* (2016.01)

(52) U.S. Cl.
CPC ............... *A23B 4/26* (2013.01); *A23L 3/358* (2013.01); *A23L 33/16* (2016.08); *A23V 2002/00* (2013.01)

(56) References Cited

OTHER PUBLICATIONS

Kim, Hyun-Jin; et al; "Characterization of Bacteriocin Produced by *Lactobacillus bulgaricus*" Journal of Microbiology and Biotechnology, 14, 503-508, 2004 (Year: 2004).*
Grewal, HS; et al; "Vinegar Production from Substandard Fruits" Biological Waste, 26, 9-14, 1988 (Year: 1988).*
Van de Guchte, M; "The complete genome sequence of *Lactobacillus bulgaricus* reveals extensive and ongoing reductive evolution" Proceedings of the National Academy of Science, 103, 9274-9279, 2006 (Year: 2006).*
Li, Tao; et al; "Solubility Study and Thermal Stability Analysis of Calcium Propionate" Chemical & Engineering Technology, 40, 1221-1230, 2017 (Year: 2017).*
Patil, SS; et al; "Production of lactic acid and fructose from media with cane sugar using mutant of *Lactobacillus delbrueckii* NCIM 2365" Letters in Applied Microbiology, 43, 53-57, 2006 (Year: 2006).*
Elli, M; et al; "Iron requirement of *Lactobacillus* spp. in completely chemically defined growth media" Journal of Applied Microbiology, 88, 695-703, 2000 (Year: 2000).*
Bar, Raphael; Gainer, John L; "Acid Fermentation in Water-Organic Solvent Two-Liquid Phase Systems" Biotechnology Progress, 3, 109-114, 1987 (Year: 1987).*
Anyasi, T.A., et al., "Application of organic acids in food preservation edited by Cesar Vargas In book: Organic acids: characteristics, properties and synthesis", 2017, Nova Science Publishers. Chapter 1, pp. 1-45.—Abstract Only.
Gomes, R.J., et al., "Acetic acid bacteria in the food industry: systematics, characteristics and applications", 2018, Food Technology and Biotechnology. 56(2), pp. 139-151.
Gonzalez-Garcia, R.A., et al., "Microbial propionic acid production. Fermentation", 2017, 3(21), pp. 1-20.
Guillamon J.M., et al., "Biology of Microorganisms on Grapes, in Must and in Wine", (2017), Acetic Acid Bacteria, pp. 43-64.—Abstract Only.
Hamed A.T., et al., "The effect of apple cider vinegar and grape vinegar on lipid profile in albino white rats", 2014, Journal of Pharmaceutical Sciences. 7(3), pp. 163-170.
Komesu A, et al., "Lactic acid production to purification: A review,", 2017, BioResource Technology 12(2), pp. 4364-4383.
Menconi, A., et al; "Effect of different concentrations of acetic, citric, and prop ionic acid dipping solutions on bacterial contamination of raw chicken skin"; Poultry Science; vol. 92 ( 8), pp. 2216-2220; Aug. 2013.
Morgan, J., et al., "The potential of apple cider vinegar in the management of type 2 diabetes", 2016, International Journal of Diabetes Research, 5(6), pp. 129-134.
Nakano, S. et al; "Efficient production of D-( − )-lactic acid from broken rice by *Lactobacillus delbrueckii* using Ca(OH)2 as a neutralizing agent"; Bioresource Technology; vol. 104, pp. 791-794; 2012—Abstract Only.
Notification of Transmittal of The International Search Report and the Written Opinion of the International Searching Authority, or the Declaration for International Application No. PCT/IN2019/050727, "An Organic Natural Microbial Inhibitor", date of mailing: Dec. 13, 2019.
Ouattara A, et al., "Production of acetic acid by acetic acid bacteria using mango juice in Burkina Faso", 2018, International Journal of Biology and Chemical Science 12(5), pp. 2309-2317.
Sharma S., "Food preservatives and their harmful effects, International Journal of Science and Research Publication", Apr. 2015, 5 (4), pp. 1-2.
Surve, A.N., et al; "Preservative effect of combinations of acetic acid with lactic or prop ionic acid on buffalo meat stored at refrigeration temperature"; Meat Science; vol. 2 9 ( 4), pp. 309-322; 1991.—Abstract Only.

\* cited by examiner (a)

(b)

ORGANIC NATURAL MICROBIAL INHIBITOR

This application is the U.S. National Stage of International Application No. PCT/IN2019/050727, filed Oct. 2, 2019, which designates the U.S., published in English, and claims priority under 35 U.S.C. § 119 or 365(c) to Indian application Ser. No. 201941021081, filed May 28, 2019. The entire teachings of the above applications are incorporated herein by reference.

FIELD OF THE INVENTION

The present invention deals with the "Organic Natural Microbial Inhibitor" produced through the eco-friendly biological fermentation technology. It is a natural and organic product with many applications in food industries for preservation. It acts as an effective antimicrobial component and pH regulator. It is an effective source for acidification of foods like pickles. It can even prevent the growth of pathogenic microbes such as *Escherichia coli, Aspergillus* sp., and even non-classical foodborne pathogens such as *Klebsiella pneumoniae*.

BACKGROUND OF THE INVENTION

In the scenario of the increased cost of living in the society, the number of people needs to work in a family and the available time for food preparation are inversely associated. Therefore, preparation of bulk amount of food at a time and its storage with various physical and chemical approaches became a common practice. Physical methods (like dehydration, UV-C radiation, freeze drying, refrigeration, etc.) and chemical preservatives (benzoic acid, potassium sorbate, etc.) have been traditionally used for food preservation. However, the latter have been found to have detrimental effects on human health (Sharma, 2015). Consequently, a "natural, organic preservative" is in demand to fulfill the requirement of healthy lifestyle without side effects in the regular consumption.

Organic acids like acetic acid, lactic acid, propionic acid, sorbic acid, and benzoic acid have been reported for their antimicrobial functions (Anyasi et al., 2017). Acetic acid has multiple uses in food preparations, beverages, and household cleaning works. It has reported health benefits to control type-2 diabetes, assisting in weight loss (Joanna and Sapha, 2016), and reduction of cholesterol (Hamed and Mater, 2014) etc. These organic acids are synthesized either by a chemical method or through the biological fermentation technology. Chemically, acetaldehyde undergoes catalytic oxidation to produce acetic acid along with formic acid and formaldehyde as byproducts. This acetic acid is separated from the byproducts by distillation and the diluted acetic acid up to 5% is coated as food grade product. Whereas, fermentation of various raw materials including ethanol, grains, and fruits using microbes stands as the biological approach. Microbial strains of family *Propionibacterium* and *Lactobacillus* are well reported for their organic acid production ability by oxidation of sugars or alcohol (Guillamón and Mas, 2017). The number of genera identified in this family is increased tremendously from two to nineteen within two decades. These groups of bacteria are well known for their applications in the food industry for the production of vinegar, cocoa, and kombucha etc. (Gomes et al., 2018).

Organic acids inhibit the microbial growth by unbalancing their pH levels. The interior neutral pH of the cytosol will be decreased by the organic acids entry and increases the acidity of the cell. This disruption of cellular metabolic processes such as ATP synthesis, replication, transcription, translation, and cell growth. Production of acetic acid, lactic acid, and propionic acid individually by microbial fermentation technology is well reported (Ouattara et al., 2018, Komesu et al., 2017, Gonzalez-Garcia et al., 2017). Many species of *Acetobacter, Lactobacillus* and *Propionibacterium* are used for the production of these organic acids in controlled conditions. However, for enhanced functionality of the preservative, a combinational production of these organic acids will be an impending alternative. In the present invention the "Organic Natural Microbial Inhibitor" is a liquid and also a powder formulation containing organic acids (mainly acetic, lactic, propionic acids and with total 7-8 organic acids) in a specific proportion for maximal microbial inhibition.

SUMMARY OF THE INVENTION

The present invention relates with the "Organic Natural Microbial Inhibitor" produced through the eco-friendly biological fermentation technology. It is a natural and organic product with many applications in food industries for preservation. It acts as an effective antimicrobial component and pH regulator. It is an effective source for acidification of foods like pickles. It can even prevent the growth of pathogenic microbes such as *Escherichia coli, Aspergillus* sp., and even non-classical foodborne pathogens such as *Klebsiella pneumoniae*.

In another embodiment of the present invention, "An Organic Natural Microbial Inhibitor" is a potent source of natural preservative in the scenario of growing health concern in the consumers. Its addition in food preparations like pickles, salads, sauces, beverages, and meat can prevent food spoilage.

In one of the embodiment, the present invention relates to the process of production of the "Organic Natural Microbial Inhibitor" from the microbial co-fermentation of natural carbohydrate sources obtained from organic non-palatable raw material like rice flour, wheat hydrolysate and corn steep liquor followed by downstream processing steps including filtration, sterilization and evaporation under vacuum at 65° C. temperature. After evaporation, the product will be in liquid form with organic acids (65-67%) and moisture (33-35%).

Further, the calcium fortified liquid product will be spray dried at a temperature of 285° C. to produce powder form of the product-organic natural microbial inhibitor.

In another embodiment of the present invention, "Organic Natural Microbial Inhibitor" is produced by the biological fermentation of two in-house developed strains—*Acetobacter aceti* NCIM 2094 and *Lactobacillus delbrueckii* NCIM 2365. The microbes are grown in appropriate standardized media for the production of the high amount of the desired organic acids in the specific proportions. These bacterial strains were originally procured from National Collection for Industrially Important Microorganisms (NCIM), at National Chemical Laboratory, Pune and were modified by way of strain improvement methods.

One of the embodiment of the present invention relates to that the main components of "Organic Natural Microbial Inhibitor" is a combination of naturally produced organic acids in liquid form and also in powder form, which includes acetic acid (58-60%), lactic acid (13-15%), propionic acid (5-6%) and other organic acids (2-3%) and calcium (20-22%) with moisture of 1% in powder form of the product.

Calcium serves as a nutritional additive. With high bioavailability, it acts as a vital source of calcium for people suffering from calcium deficiency such as hypocalcemia and osteoporosis. As compare to traditional approaches, addition of "Organic Natural Microbial Inhibitor" to food items prevents food spoilage arising from microbial contamination.

Another embodiment of the present invention relates to the addition of 0.1-1.5% of "Organic Natural Microbial Inhibitor" to food preparation which enhances the flavor along with keeping it safe from microbial contaminations. In case of meat application of Organic Natural Microbial Inhibitor increases the tenderness of the meat besides functioning as an antimicrobial preservative.

DETAILED DESCRIPTION OF THE INVENTION

Figure 1:
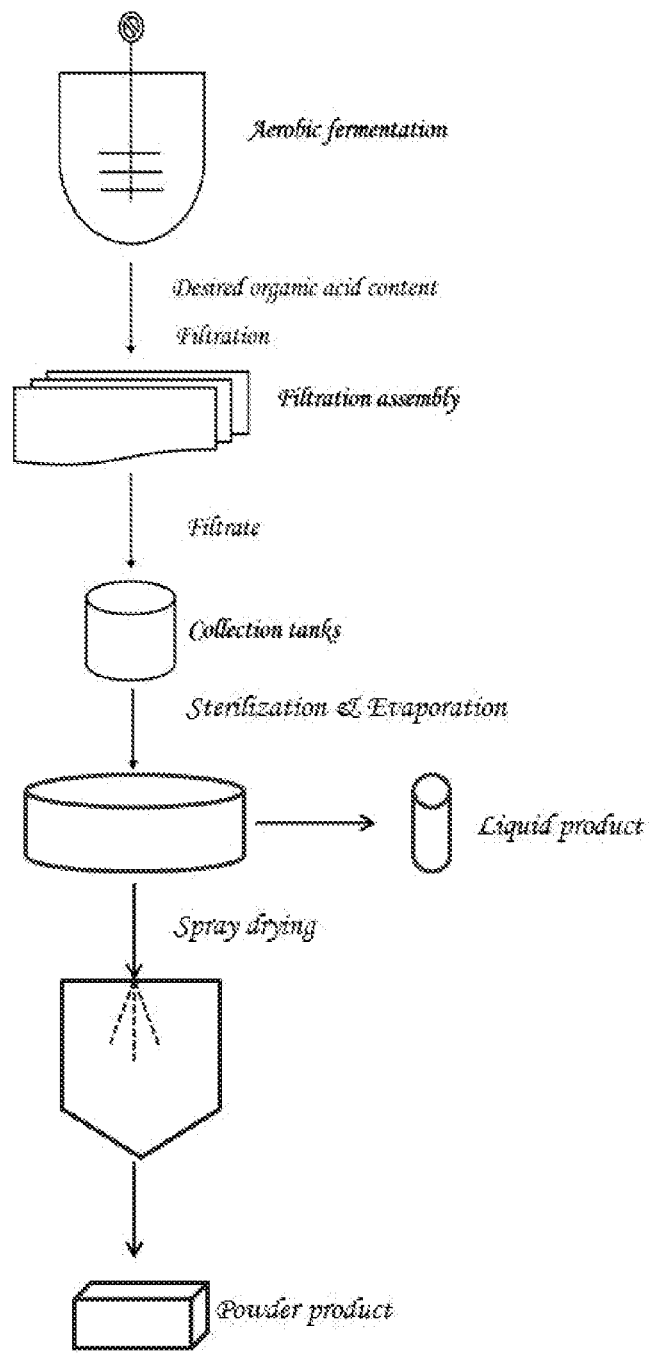
FIG. 1: Flow chart of the process of Organic Natural Microbial Inhibitor production.

The present invention relates with the "Organic Natural Microbial Inhibitor" produced through the eco-friendly biological fermentation technology. It is a natural and organic product with many applications in food industries for preservation. It acts as an effective antimicrobial component and pH regulator. It is an effective source for acidification of foods like pickles. It can even prevent the growth of pathogenic microbes such as *Escherichia coli, Aspergillus* sp., and even non-classical foodborne pathogens such as *Klebsiella pneumoniae*.

In another embodiment of the present invention, "An Organic Natural Microbial Inhibitor" can be a potent source of natural preservative in the scenario of growing health concern in the consumers. Its addition in food preparations like pickles, salads, sauces, beverages, and meat can prevent food spoilage.

In one of the embodiment, the present invention relates to the process of production of the "Organic Natural Microbial Inhibitor" from the microbial co-fermentation of natural carbohydrate sources obtained from organic non-palatable raw material like rice flour, wheat hydrolysate and corn steep liquor followed by downstream processing steps including filtration, sterilization and evaporation under vacuum at 65° C. temperature. After evaporation, the product will be in liquid form with organic acids (65-67%) and moisture (33-35%).

Further, the calcium fortified liquid product will be spray dried at a temperature of 285° C. to produce powder form of the product-organic natural microbial inhibitor.

In another embodiment of the present invention, "Organic Natural Microbial Inhibitor" is produced by the biological fermentation of two in-house developed strains—*Acetobacter aceti* NCIM 2094 and *Lactobacillus delbrueckii* NCIM 2365. The microbes are grown in appropriate standardized media for the production of the high amount of the desired organic acids in the specific proportions. These bacterial strains were originally procured from National Collection for Industrially Important Microorganisms (NCIM), at National Chemical Laboratory, Pune and were modified by way of strain improvement methods.

One of the embodiment of the present invention relates to that the main components of "Organic Natural Microbial Inhibitor" is a combination of naturally produced organic acids in liquid form and also in powder form, which includes acetic acid (58-60%), lactic acid (13-15%), propionic acid (5-6%) and other organic acids (2-3%) and calcium (20-22%) with moisture of 1% in powder form of the product. Calcium serves as a nutritional additive. With high bioavailability, it acts as a vital source of calcium for people suffering from calcium deficiency such as hypocalcemia and osteoporosis. As compare to traditional approaches, addition of "Organic Natural Microbial Inhibitor" to food items prevents food spoilage arising from microbial contamination.

Another embodiment of the present invention relates to the addition of 0.1-1.5% of "Organic Natural Microbial Inhibitor" to food preparation which enhances the flavor along with keeping it safe from microbial contaminations. In the case of meat application of Organic Natural Microbial Inhibitor in liquid form or in powder form increases the tenderness of the meat besides functioning as an antimicrobial preservative.

The present invention is further explained by the following examples. However, the present invention is not limited to these examples in any manner. The following examples are intended to illustrate the working of disclosure and not intended to take restrictively to apply any limitations on the scope of the present invention. Those persons skilled in the art will understand that the equivalent substitutes to the specific substances described herein, or the corresponding improvements are considered to be within the scope of the invention.

EXPERIMENTAL DETAILS & RESULTS

Example 1

(i) Upstream Process Parameters

A microbial consortium comprising of two lab-adapted microbial strains—*Acetobacter aceti* NCIM 2094 and *Lac-*

*tobacillus delbrueckii* NCIM 2365—were used for co-fermentation carried out at 45±2° C. on a synthetic medium with following composition as described below.

| Components | % w/v |
|---|---|
| Glucose | 18% |
| Yeast extract | 0.8% |
| Potassium dihydrogen phosphate | 0.12% |
| Diammonium hydrogen phosphate | 0.2% |
| Manganese sulphate | 0.0002% |
| Cobalt chloride | 0.0005% |
| Magnesium sulphate | 0.001% |
| Sodium chloride | 0.001% |
| Ferrous sulphate | 0.0005% |

Medium without glucose was heat sterilized at 121° C. and 15 psi for 25 min in an autoclave. Glucose was sterilized separately at 115° C. for 15 min and added aseptically to rest of the medium. All fermentation studies were carried out in 50 L stirred-tank, Stainless Steel (S.S.) bioreactors. Sterile air was flushed at 0.3 L/min into the headspace of the reactor using a 0.2 nm pore sized PTFE filter (Axiva® 200050 RI, AXIVA Sichem Biotech Pvt. Ltd., India). The pre-sterilized fermentation medium in the bioreactor was inoculated with 5% of inoculum of *Acetobacter aceti* and *Lactobacillus delbrueckii* each from 48 h grown static flask cultures at a time. Temperature and pH were set at 45° C. and 6.0 respectively with an agitation of 100 rpm. The pH was maintained and the produced organic acids are neutralized by periodical addition of sterile calcium carbonate slurry supplemented with glucose and yeast extract. This provides calcium fortification in the product, which makes the said microbial inhibitor of nutritional value.

Example 2

(ii) In-Process Monitoring of Microbial Growth and Product Yield

The cell growth during fermentation was measured in terms of optical density using UV-Vis spectrophotometer at a wavelength of 600 nm, in 3 mL of cuvettes. For dry cell weight estimation, 10-15 mL of fermentation broth was centrifuged at 10,000 rpm for 10 min in a pre-weighed empty falcon tube and dried at 60° C. under vacuum till constant weight was achieved. The dry weight of cells was calculated from the substitution of final falcon weight containing cells with the pre-weighed empty falcon weight.

Yields of the organic acids formed were analyzed in the in-process samples as well as finished product samples by High-Performance Liquid Chromatography (HPLC) based method. Analysis of organic acid content involved initial sample preparation, analysis and calculations. Around 0.1 g of test sample was dissolved in 100 mL of HPLC water. Degassing was performed with an ultra-sonicator to prepare the test sample vials. Further, the sample was filtered with a sterile 0.2 μm PTFE filter (Axiva® 200050 RI, AXIVA Sichem Biotech Pvt. Ltd., India). The samples were analyzed with reference to analytic reference standards of respective organic acids.

Further, samples were analyzed by injecting 20 μL of the prepared samples into the HPLC (Shimadzu LC2030CHT) system. Organic acids column (250×4.6 mm) was used by maintaining column temperature at 30° C. against 8 mM sulfuric acid in water mobile phase. The flow rate was maintained at 0.5 mL/min. while the total run time was 35 min. Detection was performed through UV/Vis at 215 nm.

The standards were injected using the same conditions at concentrations ranging from 2 mM to 20 mM to create a standard curve. Using a spreadsheet application, the peak areas of the standards against their concentration were plotted. Further the slope and intercept of the least square regression line were determined. Checked the line for linearity and discarded the low or high points that are not linear. The test samples were ensured that their absorbance falls within the range of the linear standard concentrations.

Using the Shimadzu Lab Solutions Software, the concentration of respective organic acids in a test sample were determined with reference to the standard calibration curve of respective organic acids in terms of difference of sample peak area and the intercept of gradient of organic acids plotted against the slope of standard curve for each of the individual organic acids.

Example 3

(iii) Downstream Processing and Product Recovery

As the maximal production of organic acids and complete utilization of glucose was achieved within 84 h of fermentation, a typical production batch was terminated between 84-90 h of fermentation. Further filtration was performed through 0.3 to 0.4-micron size cloth filters in a plate and frame filtration assembly. The filtered product was collected in collection tanks, sterilized and vacuum evaporated at 65° C. temperature. The sterilized product was then dispensed in bottles aseptically. After evaporation, the product will be in liquid form with organic acids (65-67%) and moisture (33-35%). Further, the calcium fortified liquid product will be spray dried at a temperature of 285° C. to produce powder form of organic natural microbial inhibitor. It is a combination of naturally produced organic acids, which includes acetic acid (58-60%), lactic acid (13-15%), propionic acid (5-6%) and other organic acids (2-3%) and calcium (20-22%) with moisture of 1% in powder form of the product. The production process has been depicted as a flow chart in FIG. 1.

Example 4

(iv) Microbial Growth Inhibition by Organic Natural Microbial Inhibitor

Antimicrobial activity of Organic Natural Microbial Inhibitor (ONMI) against foodborne pathogens was assessed. The product was tested against *E. coli, K. pneumoniae* and *A. flavus* cultures.

Figure 2:
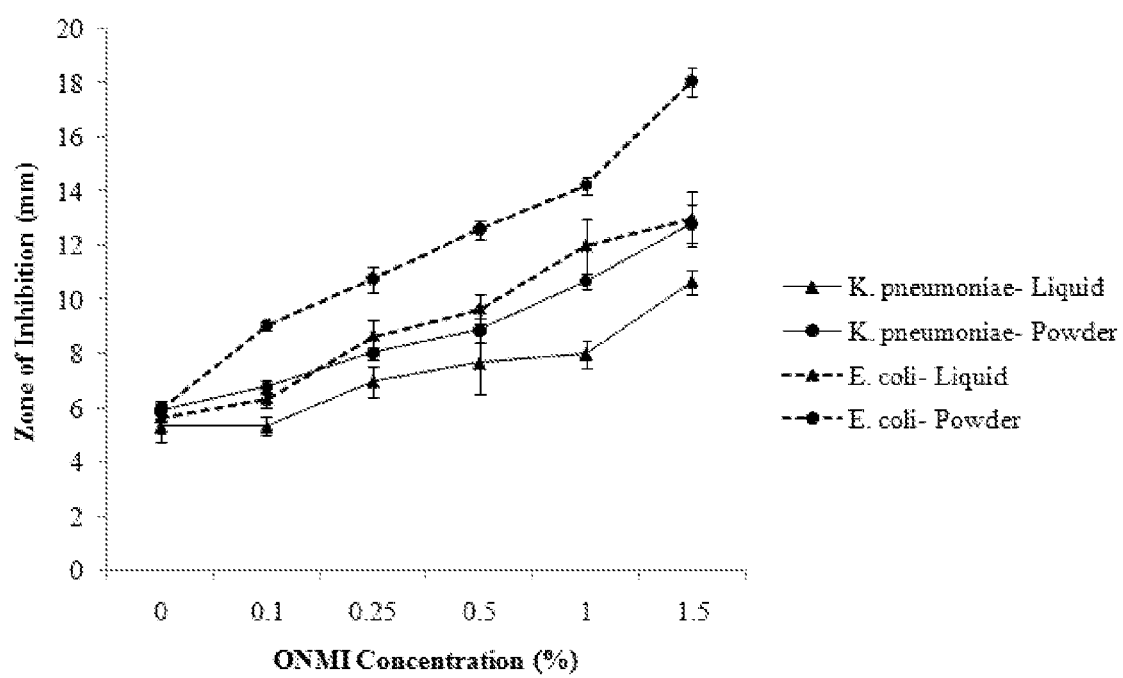
FIG. 2: (a) Graph representing the impact of ONMI in liquid and also in powder form on growth of *K. pneumoniae* and *E. coli*. Antibacterial activity was measured in terms of clear zones of inhibition against each concentration of ONMI. (b) The zone of inhibition against *K. pneumonia* (i) and *E. coli* (ii) at 0.1% and 1.5% ONMI concentrations, respectively. Tetracycline was used as positive control (PC) and sterile water was used as negative control (NC).
Figure 2:
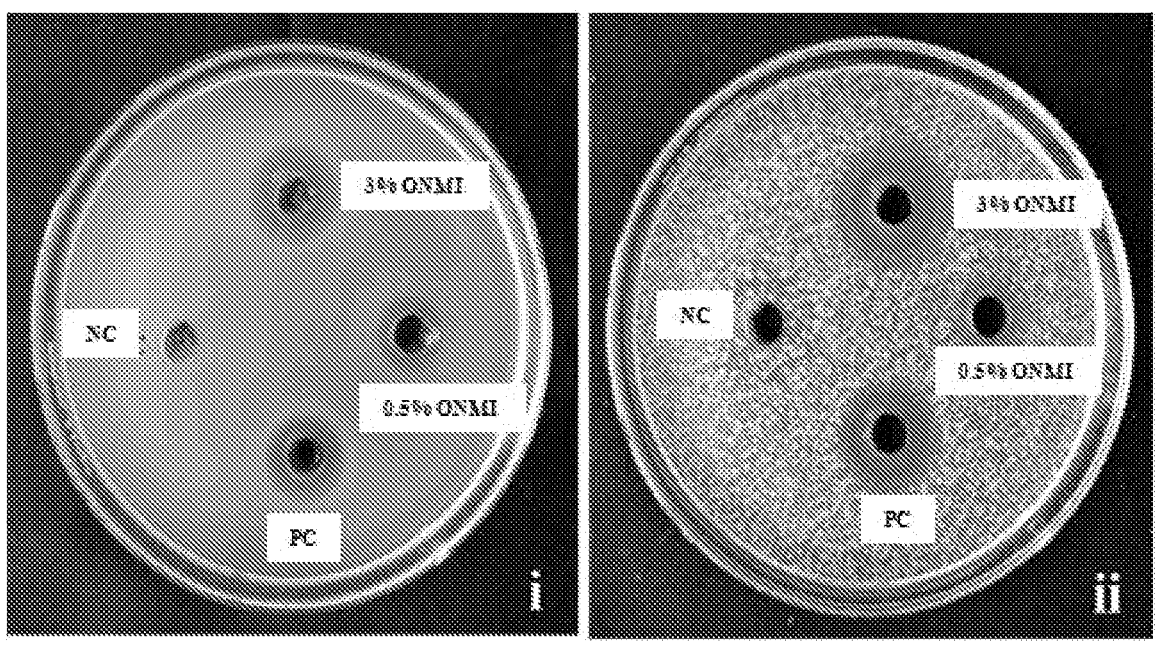

Antibacterial activity of ONMI was evaluated by agar well diffusion assay against the Gram-negative human pathogenic bacteria *Klebsiella pneumoniae* (KJ938546) and *Escherichia coli* (MCC 2412). Bacterial inoculants were prepared in nutrient broth and the turbidity was adjusted to 0.5 McFarland standards. Each test organism (100 μL) was mixed with cooled Mueller Hinton agar medium and poured into 80 mm Petri dishes. Wells were cut and ONMI in liquid as well as in powder form samples were prepared at different concentrations ranging from 0.1%, 0.25%, 0.5%, 1%, and 1.5% were added in the wells. The plates were incubated at 37° C. for 24 h and the zone of inhibition was measured (FIG. 2a, b). Tetracycline @ 1 mg/mL was used as positive control. Sterile water was used as negative control. We observed that 0.1% ONMI was only very slightly effective against *E. coli* and *K. pneumoniae*. However, as the concentration was increased, an increase in growth inhibition was observed, with maximum activity observed at 1.5% in either case. The activity was comparable to that shown by the antibiotic tetracycline.

Figure 3:
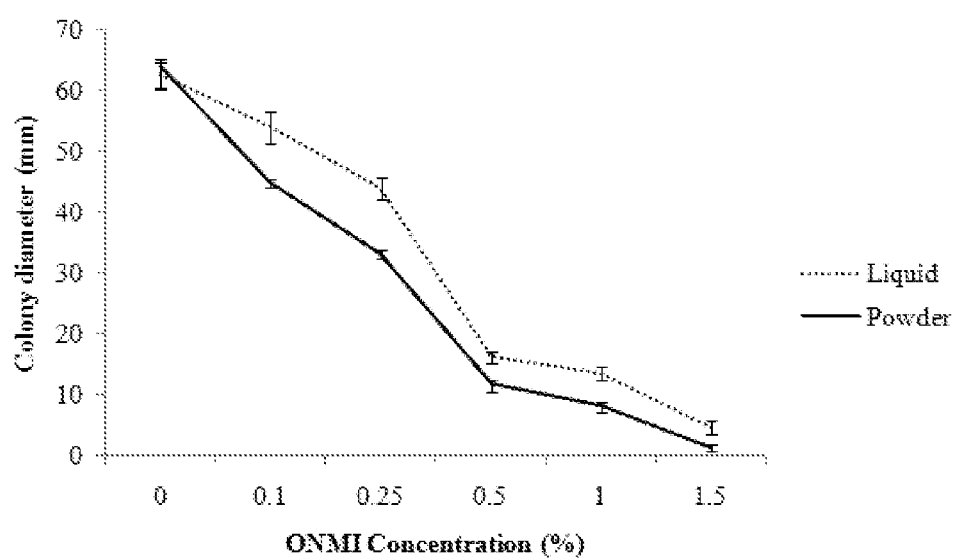
FIG. 3: Impact of ONMI in liquid and also in powder form on the fungal growth. Different concentrations of ONMI were tested against the fungus *A. flavus* and growth inhibition was measured in terms of increase in colony diameter after 6 days incubation. Maximum growth was observed in the plates without ONMI in liquid and also in powder form, no growth was observed in medium plates supplemented with 1.5% ONMI in liquid and also in powder form. In general, increase in ONMI concentration resulted in decreased fungal growth.

Antifungal activity was assayed against *Aspergillus flavus* KDP3, a fungus commonly responsible for spoilage of food and preserved meat products. Potato dextrose agar medium was prepared in separate flasks and autoclaved. After cooling to 60° C., ONMI liquid or powder form samples were added to each flask individually to yield final concentrations of 0.1%, 0.25%, 0.5%, 1%, and 1.5%. These ONMI supplemented media were poured in petri dishes and allowed to solidify. 3 mm discs were cut from the periphery of a 5 days old culture of *A. flavus* and placed at the centre of the plate. The plates were then sealed and placed in an incubator at 28° C. for 6 days. Fungal growth at each concentration was measured in terms of increase in colony diameter (mm) and was assessed at the end of incubation period (FIG. 3). The study showed that even lower concentrations of liquid or powder ONMI were effective in significantly inhibiting fungal growth; while at the maximum inhibition was observed at 1.5% where the fungus failed to propagate completely.

Example 5

(v) Meat Samples Testing With Organic Natural Microbial Inhibitor

Figure 4:
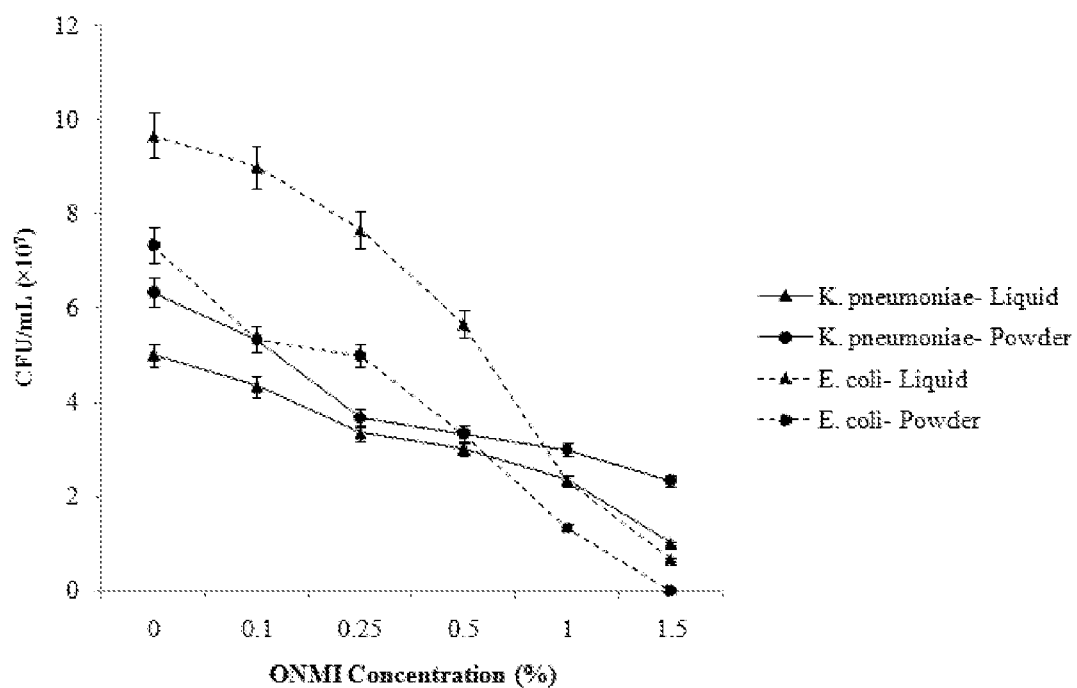
FIG. 4: Impact of ONMI in liquid and also in powder form on microbial growth in meat samples. Highest colony count ($10^7$) was recorded in non-treated samples (0% ONMI in liquid and also in powder form), whereas lowest count (10) was observed in sample treated with 1.5% ONMI in liquid and also in powder form.

Further, the impact of ONMI liquid or powder form on growth of microbial contaminants in meat samples was assayed. Raw meat chunks were dipped in ONMI samples prepared in water solution at different concentrations ranging from 0.1 to 1.5%, air dried briefly and stored in plastic bags at 27° C. and 10° C. The treated samples of meat were labelled as 'Test'. Meat chunks without ONMI treatment were taken as 'Control'. After 7 days, the samples stored at 27° C. were analysed for growth of the test pathogenic microorganisms *K. pneumoniae* and *E. coli*. One gram of the each 6 'Test' samples and 'Control' sample were macerated separately using pestle and mortar and collected in respective test tubes containing 9 mL saline water and vortexed for 10 min. Microbial growth was then assessed using serial dilution technique on nutrient agar plates. Dilutions of up to $10^9$ were prepared. Plates were observed for the presence of bacterial colonies at each concentration (FIG. 4). Bacterial growth was enumerated in terms of colony forming units per mL of solution (CFU/mL) after 24-48 h incubation at 30° C. It was observed that the 'Control' meat sample had the highest colony count of $10^7$ CFU/mL for *E. coli* and $10^6$ CFU/mL for *K. pneumoniae* in both liquid and powder form of ONMI. 'Test' samples exhibited lower colony count, with highest count of $10^5$ CFU/mL for *E. coli* and $10^4$ CFU/ mL for *K. pneumoniae* at 0.1% ONMI and lowest colony count of 10 for each of the two microbial species at 1.5% ONMI.

Figure 5:
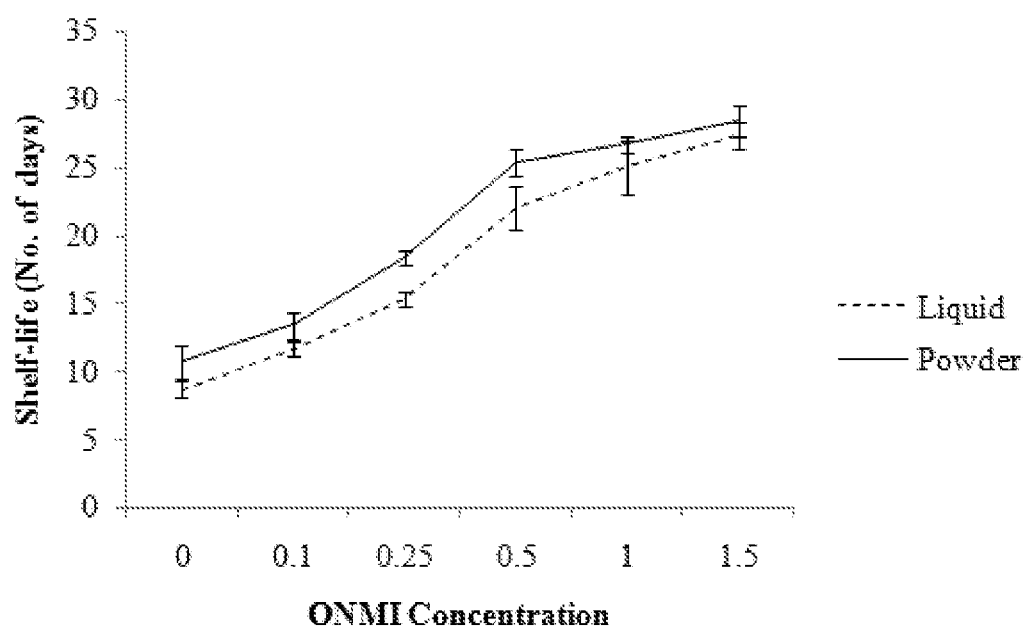
FIG. 5: Shelf-life assessment of meat samples treated with different ONMI in liquid and also in powder form concentrations. While the Control samples showed microbial growth just after 6 days of storage, samples with ONMI @ 1.5% con. did not exhibit any growth even after 28 d.

In meat samples stored at 10° C., untreated 'Control' and 'Test' samples were checked every 24 h for microbial growth using the aforementioned methodology. It was observed that microbial growth (either *E. coli* and/or *K. pneumoniae*) was first observed in 'Control' samples on $6^{th}$ day of storage. Whereas, in 'Test' samples, treatment with 1.5% ONMI resulted in microbial growth after 28 d of storage (FIG. 5). In general, the microbial growth exhibited an inversely proportional relationship, with an increase in ONMI concentration resulting in decreased microbial growth irrespective of storage temperature checked. All the experiments were repeated thrice and the data was statistically analysed.

INDUSTRIAL APPLICABILITY OF THE INVENTION

"An Organic Natural Microbial Inhibitor" acts as an effective preservative in the storage of pickles, salads, beverages, and meat etc. The targeting areas of this product are restaurants, processed food industries including beverages, and meat industries. "An Organic Natural Microbial Inhibitor" enhances the flavor and tenderness in case of the meat. In addition, it is a pH regulator and keeps the food free from microbial contaminations with its antimicrobial properties.

REFERENCES CITED

Anyasi T A, Jideani A, Edokpayi J N, Anokwuru C P (2017) Application of organic acids in food preservation edited by Cesar Vargas In book: Organic acids: characteristics, properties and synthesis, Nova Science Publishers. Chapter 1, pp 1-45.

Gomes R J, Borges M F, Rosa M F, Castro-Gómez R J H, Spinosa W A (2018) Acetic acid bacteria in the food industry: systematics, characteristics and applications. Food Technology and Biotechnology. 56(2), pp: 139-151.

Gonzalez-Garcia R A, McCubbin T, Navone L, Stowers C, Nielsen L K, and Marcellin E (2017) Microbial propionic acid production. Fermentation, 3(21), pp: 1-20.

Guillamon J M and Mas A (2017) Acetic Acid Bacteria. In: König H., Unden G., Fröhlich J. (eds) Biology of Microorganisms on Grapes, in Must and in Wine. Springer, Cham pp 43-64.

Hamed A T and Mater R A (2014) The effect of apple cider vinegar and grape vinegar on lipid profile in albino white rats. Journal of Pharmaceutical Sciences. 7(3), pp163-170.

Joanna M and Sapha M (2016) The potential of apple cider vinegar in the management of type 2 diabetes, International Journal of Diabetes Research, 5(6), pp: 129-134.

Komesu A, Oliveira J A Rd, Martins L H dS, Maciel, M R W, and Filho M R (2017). "Lactic acid production to purification: A review," BioResource Technology 12(2), pp: 4364-4383.

Ouattara A, Somda K M, Ouattara A T C, Traore S A, and Ouattara S A (2018) Production of acetic acid by acetic acid bacteria using mango juice in Burkina Faso. International Journal of Biology and Chemical Science 12(5), pp: 2309-2317.

Sharma S (2015) Food preservatives and their harmful effects, International Journal of Science and Research Publication, 5 (4), pp: 1-2

We claim:
1. An organic microbial inhibitor comprising:
a combination of 58-60% acetic acid, 13-15% lactic acid, 5-6% propionic acid, 2-3% one or more additional organic acids, and 20-22% calcium,
wherein the microbial inhibitor is produced by microbial co-fermentation of carbohydrates obtained from non-palatable raw material rice flour, wheat hydrolysate and corn steep liquor, using a microbial source comprising a bacterial consortium of *Acetobacter aceti* NCIM 2094 and *Lactobacillus delbrueckii* NCIM 2365, wherein the microbial inhibitor is in liquid form or in powder form.

2. A process for producing an organic microbial inhibitor as claimed in claim 1, comprising co-fermenting carbohydrates obtained from organic non-palatable raw material rice flour, wheat hydrolysate and corn steep liquor, using a microbial source comprising a bacterial consortium comprising *Acetobacter aceti* NCIM 2094 and *Lactobacillus delbrueckii* NCIM 2365 to produce the organic microbial inhibitor;

periodically adding a calcium source to the co-fermenting process to fortify the microbial inhibitor with calcium;

filtering the organic microbial inhibitor to produce a filtrate comprising the organic microbial inhibitor;

sterilizing the filtrate and then evaporating moisture from the filtrate to produce a liquid form of the organic microbial inhibitor; and optionally spray drying the sterilized liquid to produce the organic microbial inhibitor in powder form.

3. The process as claimed in claim 2, wherein the co-fermenting is carried out on a synthetic medium comprising: 18% glucose, 0.8% yeast extract, 0.12% potassium dihydrogen phosphate, 0.2% diammonium hydrogen phosphate, 0.0002% manganese sulfate, 0.0005% cobalt chloride, 0.001% magnesium sulfate, 0.001% sodium chloride and 0.0005% ferrous sulfate (% w/v).

4. The process as claimed in claim 3, wherein the synthetic medium is prepared by heat sterilizing the synthetic medium in the absence of glucose at 121° C. and 15 psi for 25 min.; separately autoclaving the glucose at 115° C. for 15 min; and then adding the autoclaved glucose aseptically to the sterilized synthetic medium.

5. The process as claimed in claim 2, wherein the co-fermenting is carried out in 50 L stirred-tank, Stainless Steel (S.S.) bioreactor in batch mode at a temperature of 45±2° C., pH of 6.0±0.2, agitation at 100 rpm and sterile air 0.3 L/min.

6. The process as claimed in claim 5, wherein the co-fermenting is terminated between 84-90 hours.

7. The process as claimed in claim 2, wherein the filtering is carried out through a 0.3 to 0.4-micron size cloth filter in a plate and frame filtration assembly, followed by sterilization of filtrate, and evaporation carried out under vacuum at 65° C.

8. The organic microbial inhibitor as claimed in claim 1, wherein the microbial inhibitor is in liquid form.

9. The organic microbial inhibitor as claimed in claim 8, wherein the liquid form of the microbial inhibitor comprises naturally produced organic acids (65-67%) and moisture (33-35%).

10. The process as claimed in claim 2, wherein the calcium fortified organic microbial inhibitor in liquid form is spray dried at a temperature of 285° C. to produce a powder form of the microbial inhibitor.

11. The organic microbial inhibitor as claimed in claim 1, wherein the microbial inhibitor is in powder form.

12. The organic microbial inhibitor as claimed in claim 11, wherein the powder form of the organic microbial inhibitor is a combination of naturally produced organic acids (79%), calcium (20%) with moisture of 1%.

13. A method of keeping food products safe from microbial contamination comprising adding 0.1% to 1.5% of the organic microbial inhibitor of claim 1 to a food or food product, wherein the addition provides for flavor enhancement and improved safety from microbial contamination.

14. The method according to claim 13, wherein the food product is pickles, salads, beverages or meat.

* * * * *